United States Patent [19]

Fung et al.

[11] Patent Number: 5,646,181
[45] Date of Patent: Jul. 8, 1997

[54] METHOD AND COMPOSITIONS FOR TREATING IMPOTENCE

[75] Inventors: Ho-Leung Fung, Getzville; John Anthony Bauer, Williamsville, both of N.Y.

[73] Assignee: Research Foundation of State University of New York, Albany, N.Y.

[21] Appl. No.: 432,892

[22] Filed: May 2, 1995

Related U.S. Application Data

[63] Continuation-in-part of Ser. No. 199,280, Mar. 1, 1994, Pat. No. 5,489,610, which is a continuation-in-part of Ser. No. 908,224, Jul. 2, 1992, Pat. No. 5,278,192.

[51] Int. Cl.⁶ .................................................. A61K 31/04
[52] U.S. Cl. ........................ 514/506; 514/509; 514/645; 514/740; 514/462; 514/470; 558/488
[58] Field of Search ........................... 514/506, 462, 514/509, 470, 645, 740; 558/488

[56] References Cited

U.S. PATENT DOCUMENTS

| | | | |
|---|---|---|---|
| 3,213,147 | 10/1965 | Feuer et al. | 260/644 |
| 3,760,012 | 9/1973 | Larkin | 260/644 |
| 4,112,115 | 9/1978 | Coghlan | 424/300 |
| 4,450,175 | 5/1984 | Warshaw | 424/349 |
| 5,049,694 | 9/1991 | Bron et al. | 558/480 |
| 5,059,603 | 10/1991 | Rubin | 514/264 |
| 5,278,192 | 1/1994 | Fung et al. | 514/645 |

FOREIGN PATENT DOCUMENTS

WO94/0110  1/1994  WIPO.

OTHER PUBLICATIONS

Chemical Abstracts 71:79612, "Toxicology, Metabolism, and Pharmacologic Properties of Propylene Glycol 1,2-Dinitrate".

Chemical Abstracts 78:135650, "Nitrites of Glycols and Their Derivatives".

Truss, et al., *Urology*, vol. 44, No. 4, pp. 553–556 (1994).

Wang, et al., *J. Urology*, vol. 151, pp. 234–237 (1994).

Hellstrom, et al., *J. Urology*, vol. 151, pp. 1723–1727 (1994).

Anderson, *Annals Pharm.*, vol. 27, pp. 1203–1205 (1993).

Nunez, et al., *J. Urology*, vol. 150, pp. 1241–1243 (1993).

Lerner, et al., *J. Urology*, vol. 149, pp. 1246–1255 (1993).

Chen, et al., *J. Urology*, vol. 147, pp. 1124–1128 (1992).

Rajfer, et al., *New. England J. Med.*, vol. 326, No. 2, pp. 90–94 (1992).

Steif, et al., *J. Urology*, vol. 148, pp. 1437–1440 (1992).

Knispel, et al., *Urol. Res.*, vol. 20, pp. 253–257 (1992).

Williams & Wilkins, *The Lancet*, vol. 340, No. 8824, pp. 882–883 (1992).

Patent Abstracts of Japan, *Tape Preparation*, vol. 12, No. 467 (1988).

Talley, et al., *Annals of Int. Med.*, vol. 103, No. 5, p. 804 (1985).

Derwent Abstracts, Fribolin, et al., *Medicaments for Treating Cardiogenic Shock*, 78-35053A (1978).

Hollister, *Life Sciences*, vol. 17, No. 5, pp. 661–668.

*Primary Examiner*—Frederick Krass
*Attorney, Agent, or Firm*—Kirschstein, et al.

[57] ABSTRACT

Pharmaceutical compositions in topical or parenteral form containing organic nitrites are effective in treating male impotence and erectile dysfunction through topical or intracavernosal administration to the penis. Methods of treatment utilizing the nitrite-containing compositions are also disclosed, as are certain novel organic nitrite compounds.

7 Claims, 10 Drawing Sheets

METHOD AND COMPOSITIONS FOR TREATING IMPOTENCE

CROSS-REFERENCE TO RELATED APPLICATIONS

This application is a continuation-in-part of application Ser. No. 08/199,280, filed Mar. 1, 1994, now U.S. Pat. No. 5,489,610 which is a continuation-in-part of application Ser. No. 07/908,224, filed Jul. 2, 1992, (now U.S. Pat. No. 5,278,192).

BACKGROUND OF THE INVENTION

1. Field of the Invention

This invention relates to methods and compositions for treating male impotence and erectile dysfunction.

2. Description of the Prior Art

The process of erection is generally a selective vasodilation of the spongy penile tissue and corpus cavernosum and reductions in outflow, leading to blood pooling, elevation of intra-cavernous pressure, and therefore erection.

Conventional therapies for impotence or erectile dysfunction primarily include local administration of vascular smooth muscle relaxants, for example papaverine or prostaglandin E1, or α-adrenoceptor antagonists, such a phentolamine, resulting in penile erection because of an increase in arterial inflow of blood, distension of sinusoids and possible restriction of venous outflow. Thus, intracavernous injection of vasoactive drugs offers impotent patients a form of therapeutic management, and allows one of the tests for differential diagnosis between vasculogenic and other etiologic forms of impotence. Papaverine and prostaglandin E1 are also used in the assessment of pharmacological response of penile erectile tissues under experimental conditions (see Chen et al., *J. Urol.*, 147:1124–1128, 1992).

Other pharmaceutical treatments for impotence have been practiced in the prior art. These include systemic administration of male hormonal preparations such as methyltestosterone and testosterone esters, as well as administration of various naturally occurring plant extracts believed to have aphrodisiac properties, such as yohimbine, ginseng, strychnine and the like. Non-pharmacological therapeutic modalities for impotence include the surgical implantation of penile prostheses and the use of tourniquet-like devices which fit tightly around the shaft of the penis and restrict the flow of blood through the surface veins and the deeper dorsal vein to prolong erection.

All of the foregoing prior art treatment methods suffer from obvious and serious disadvantages. The injection of papaverine and other vasoactive drugs meets with variable success and variable duration of response, and repeated injections into the penis can be painful and traumatic. In some patients these agents cause priapism (undesirable sustained erection), which can lead to structural damage to the organ. The administration of methyltestosterone or testosterone esters may cause toxic effects or inhibit endogenous testosterone formation and spermatogenesis. Orally administered aphrodisiac substances are of marginal and erratic efficacy, and some have significant adverse side effects. The use of surgical implants or tourniquet-like devices can lead to serious problems of infection and trauma, and cause discomfort to both male and female partners.

Several recent studies have shown the obligatory role of nitric oxide for the erection process (see for example Rajfer et al., *N. Eng. J. Med.*, 326:90–94, 1992). Stimulation of the local nerve leads to production of NO and vasorelaxation, leading to erection. Because of the importance of NO in erection, NO donors may have utility for the treatment of impotence. Hence, it has recently been proposed to use nitric oxide donors such as nitroglycerin (see U.S. Pat. No. 5,059,603) and linsidomine chlorhydrate (see *Urology*, 44:553–556, 1994) applied topically or via intracavernosal injection to treat impotence and erectile dysfunction.

The use of these and other nitric oxide donors proposed in the literature for treatment of impotence is also less than completely satisfactory. Nitroglycerin, even when applied topically as an ointment, has received variable responses and may cause severe headaches (see Talley et al., *Ann. Int. Med.*, 103:804, 1985). Of even greater concern is that systemic absorption of most vasoactive agents causes significant reductions in systemic blood pressure resulting in side effects such as light-headedness, increased heart rate, etc., and sometimes causing activation of the sympathetic nervous system leading directly to de-tumescence. For these reasons, the use of nitroglycerin for the treatment of impotence is less than ideal.

Improved pharmaceutical compositions and methods are required for treatment of impotence while avoiding the serious adverse effects experienced with prior art treatment modalities.

SUMMARY OF THE INVENTION

The present invention resides, briefly stated, in the local (topical or intracavernosal) administration of organic nitrites to the penis to induce and maintain erection with selective local (cavernosal) vasodilation and little or no "downstream" systemic vasodilating effects. The organic nitrites which may be used in the present invention include those disclosed in co-pending parent application Ser. No. 08/213,542, filed Mar. 15, 1994, now abandoned, as well as additional, novel organic nitrite compounds disclosed and described herein. The invention also comprehends nitrite-containing topical and parenteral pharmaceutical compositions for treatment of impotence.

DETAILED DESCRIPTION OF THE INVENTION

Figure 1:
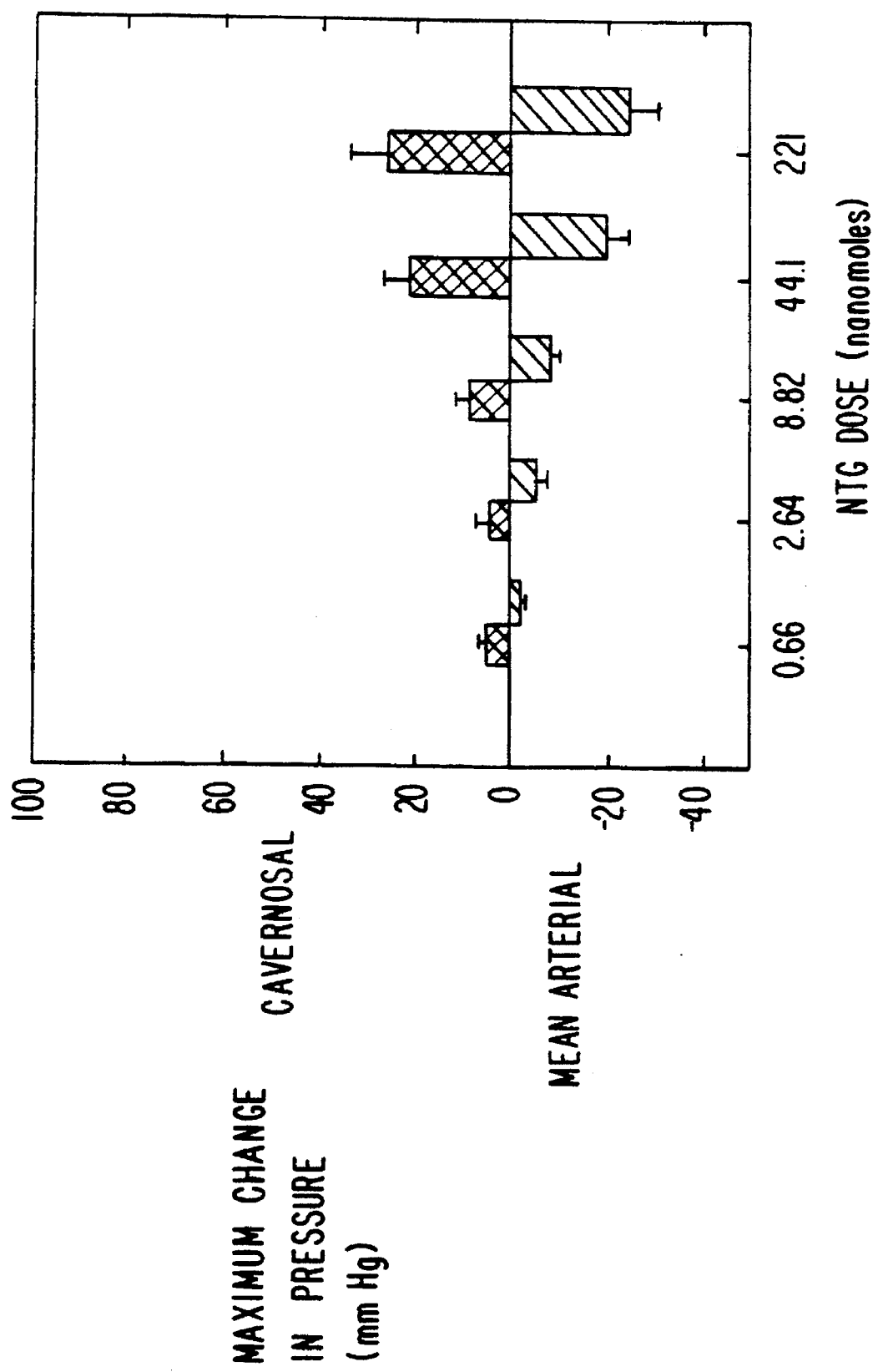
FIG. 1 is a bar graph illustrating the effects of intracavernosal injection of nitroglycerin (NTG) in anesthetized rats on cavernosal blood pressure and arterial blood pressure (as measured in the left femoral artery).

The present invention pertains to the local administration of vasodilating organic nitrites to the penis, either by application of nitrite-containing topical pharmaceutical compositions (e.g., ointments, creams, gels, lotions, liquids, sprays and the like) or by intracavernosal injection of parenteral nitrite-containing compositions, for effective treatment of male impotence and erectile dysfunction in humans.

It has been discovered that the use of organic nitrites in the treatment of impotence and related conditions yields unexpected therapeutic advantages in comparison with vasodilating agents used for the same purposes in the prior art, including closely related vasodilators such as nitroglycerin. Chief among these unexpected advantages are an increase in the degree of tumescence achieved and substantial absence of systemic vasodilating effects, resulting in a smaller drop in systemic blood pressure than occurs with prior art vasodilators. The combination of these effects renders the organic nitrites more effective and safer than other vasodilators previously used to induce or maintain erection. The organic nitrites also are far less prone to causation of adverse side effects such as the severe headaches that can be caused by nitroglycerin, because of the smaller effect on the rest of the body.

Topical pharmaceutical compositions containing one or a mixture of organic nitrites for use in the present invention preferably contain at least one active nitrite ingredient in a concentration sufficient to supply from about 0.1–20 mg of active nitrite ingredients per dose (e.g., per application of about 50 to 500 mg of topical composition), in a pharmaceutically acceptable topical carrier or vehicle. Such vehicle can be in the form of an ointment, gel, cream, lotion, liquid, spray, or any other form known to those skilled in the pharmaceutical and formulation arts. The vehicles used in the topical compositions may contain any conventional solvents, emollients, humectants, surfactants, opacifying and coloring agents, penetration enhancers, and other additives commonly used in topical vehicles. The inactive ingredients in the topical compositions should be chemically compatible with the active nitrite ingredients and of low irritation potential so that the compositions can be safely applied to the sensitive areas of the penis.

Topical carriers useful for formulating nitrite-containing compositions include, for example, ointment, gel and cream bases containing white petrolatum, paraffin wax, caprylic/capric diglyceryl succinate, diisopropyl adipate and/or ethoxydiglycol.

Examples of topical carriers suitable for use with the organic nitrites of the present invention are set forth in U.S. Pat. No. 5,059,603, the disclosures of which are incorporated herein by reference.

The organic nitrites may also be incorporated into tapes and patches to be applied to the penis. These drug-releasing tapes and patches may be prepared in accordance with the technology widely utilized for slow-release transdermal vehicles containing cardiovascular (e.g., anti-anginal) drugs.

A number of different transdermal products which can employ the organic nitrites in accordance with the invention are described by Curtis Black, "Transdermal Drug Delivery", U.S. pharmacist, Nov. 1982, pp. 49–75, which disclosure is hereby incorporated by reference. Additionally, exemplary patents relating to delivery systems include U.S. Pat. Nos. 4,191,015; 3,742,951; 4,191,015; 3,742,951 and 4,262,003 which disclose using penetration enhancers to control delivery rates, which disclosures are hereby incorporated by reference.

Moreover, the topical nitrite-containing compositions, particularly in the form of ointments or gels, can be coated onto the inside of a condom, for example, a latex condom, which can be applied to the penis in conventional fashion. Such mode of administration serves the dual purposes of promoting erection and providing a contraceptive and disease-transmission barrier during intercourse. Alternatively, devices such as condoms and penis rings can be impregnated with the nirite-containing compositions to achieve a comparable effect.

Parenteral vehicles for nitrite-containing compositions in accordance with the invention include solutions or dispersions of one or a mixture of organic nitrites in a pharmaceutically acceptable parenteral carrier. Such carriers may include non-aqueous solvents or diluents, e.g., ethanol, benzyl alcohol or propylene glycol, and may also include as solvents, diluents or stabilizers, glycerine, povidone, lecithin, sorbitan monooleate or trioleate, polysorbate 80, peanut oil, castor oil, and other triglycerides. Lipid emulsion carriers may also be employed. The parenteral composition should have a sufficient concentration of active nitrite ingredient to provide about 0.01–0.75 mg of nitrite per injectable dose, said dose being about 0.1 to 0.5 ml of parenteral composition.

Organic nitrites which can be used in the present invention include any organic nitrite ester, i.e., any ester of nitrous acid and an organic alcohol, provided that the starting alcohol is not toxic and does not interfere with or counteract the vasodilating effect of the nitrite. Such organic nitrites can include, for example, straight or branched chain alkyl nitrites, arylalkyl nitrites, cycloalkyl nitrites, haloalkyl or halocycloalkyl nitrites and heterocyclic nitrites, as well as di- and trinitrite analogs of the foregoing. The di- and trinitrite esters may be produced by reacting nitrous acid with the appropriate diols or triols or by forming partial esters of polyols such as pentaerythritol. Preferred nitrites containing alkyl groups are those in which the alkyl is $C_1$–$C_{10}$.

Illustrative examples of organic nitrites which may be useful in the method of the invention are shown below.

| Structure | Formula | Name |
|---|---|---|
| 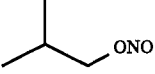 | C₄H₉NO₂ | isobutyl nitrite |
| 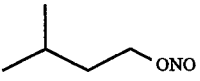 | C₅H₁₁NO₂ | isoamyl nitrite |
|  | C₃H₆N₂O₄ | 1,3-propane dinitrite |
| 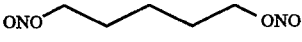 | C₅H₁₀N₂O₄ | 1,5-pentane dinitrite |
|  | C₇H₁₄N₂O₄ | 1,7-heptane dinitrite |
| 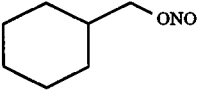 | C₇H₁₃N₂O₄ | cyclohexylmethyl nitrite |
| 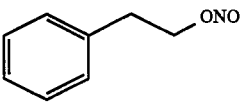 | C₈H₉NO₂ | 2 phenylethyl nitrite |
| 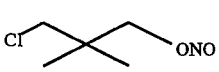 | C₅H₁₀ClNO₂ | 3-chloro-22-dimethylpropyl nitrite |
| 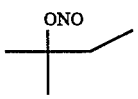 | C₅H₁₁NO₂ | tert-amyl nitrite |
| 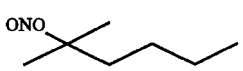 | C₇H₁₅NO₂ | 2-hexanol, 2-methyl, nitrite |
| 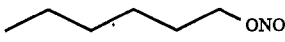 | C₆H₁₃NO₂ | hexyl nitrite |
| 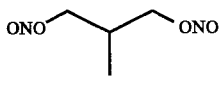 | C₄H₈N₂O₄ | 2-methyl-1,3-propane dinitrite |
|  | C₅H₁₀N₂O₄ | 2,2-dimethyl-1,3-propane dinitrite |
| 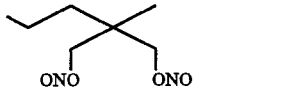 | C₇H₁₄N₂O₄ | 2-methyl-2-propyl-1,3-propane dinit. |
| 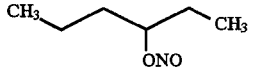 | C₆H₁₃NO₂ | 3-hexyl nitrite |
| 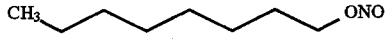 | C₈H₁₇NO₂ | octyl nitrite |
| 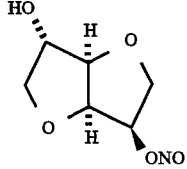 | C₆H₉N₂O₅ | isosorbide 5-mononitrite |
| 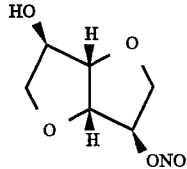 | C₆H₉N₂O₅ | isoidide 5-mononitrite |

-continued

| Structure | Formula | Name |
|---|---|---|
| (bicyclic diol mononitrite structure with HO, H, O, ONO) | $C_6H_9N_2O_5$ | isomannide 5-mononitrite |
| HOCH$_2$–C(CH$_2$OH)(CH$_2$OH)–CH$_2$ONO | $C_5H_{11}NO_5$ | pentaerythrityl mononitrite |
| HOCH$_2$–C(CH$_2$OH)(CH$_2$ONO)–CH$_2$ONO | $C_5H_{10}N_2O_6$ | pentaerythrityl dinitrite |
| HOCH$_2$–C(CH$_2$ONO)(CH$_2$ONO)–CH$_2$ONO | $C_5H_9N_3O_7$ | pentaerythrityl trinitrite |
| ONOCH$_2$–C(CH$_2$ONO)(CH$_2$ONO)–CH$_2$ONO | $C_5H_8N_4O_8$ | pentaerythrityl tetranitrite |
| (CH$_3$)$_2$CHCH$_2$CH(ONO)CH$_3$ | $C_6H_{13}NO_2$ | 4-methyl-2-pentyl nitrite |
| (CH$_3$)$_2$CHCH$_2$CH$_2$CH$_2$ONO | $C_6H_{13}NO_2$ | 4-methyl-1-pentyl nitrite |
| CH$_3$(CH$_2$)$_4$CH(ONO)CH$_3$ | $C_7H_{15}NO_2$ | 2-heptyl nitrite |
| CH$_3$(CH$_2$)$_3$C(ONO)(CH$_3$)CH$_3$ | $C_7H_{15}NO_2$ | 2-methyl-2-hexyl nitrite |
| CH$_3$(CH$_2$)$_4$CH(ONO)CH$_2$CH$_3$ | $C_8H_{17}NO_2$ | 3-octyl nitrite |
| CH$_3$CH$_2$CH$_2$C(ONO)(CH$_3$)CH$_3$ | $C_6H_{13}NO_2$ | 2-methyl-2-pentyl nitrite |
| (CH$_3$)$_2$CHCH$_2$CH$_2$CH(ONO)CH$_3$ | $C_7H_{14}NO_2$ | 5-methyl-2-hexyl nitrite |
| (CH$_3$)$_2$CHCH$_2$CH$_2$CH$_2$CH(ONO)CH$_3$ | $C_8H_{16}NO_2$ | 6-methyl-2-heptyl nitrite |
| ONOCH$_2$–CH(ONO)–CH$_2$ONO | $C_3H_5N_3O_6$ | glyceryl trinitrite |
| R–CH(R')–R" | $C_3H_7NO_4$ | glyceryl mononitrite |

1-nitrite: R = ONO; R' = R" = OH or
2-nitrite: R = R" = OH; R' = ONO

Of the above-listed organic nitrites, the three dinitrite compounds, i.e., 1,3-propane dinitrite, 1,5-pentane dinitrite and 1,7-heptane dinitrite are novel compounds. These dinitrites may be prepared by adding a solution of 4N hydrochloric acid to a solution of sodium nitrite and the appropriate diol (for example, 1,7-heptane diol) in water at room temperature. After addition of the hydrochloric acid, the reaction mixture is cooled and concentrated sulfuric acid added. After complete addition of the sulfuric acid, the two-phased solution is stirred with cooling and then decanted. The top oily layer is separated, diluted (e.g., with methylene chloride) and washed, for example with a saturated solution of sodium bicarbonate. The resulting organic phase is separated, dried, filtered and concentrated in vacuo. The oily residue sustained is distilled under high vacuum to yield the desired dinitrite product.

The following examples are presented to further illustrate the compositions and methods of the present invention and the novel organic nitrite compounds which may be effectively used, among others, in practicing the novel method. These examples also demonstrate the remarkable ability of the organic nitrite-containing compositions to induce erection in tests using accepted animal models while at the same time not inducing generalized systemic vasodilation. These examples should not be viewed, however, as providing compounds, compositions, formulations or methods of administration which must be practiced exclusively in order to come within the present invention.

EXAMPLE 1

Preparation of 1,7-Heptane Dinitrite

A solution of 4N hydrochloric acid (38.0 ml) was added dropwise to a one-necked 1000 ml round-bottomed flask containing a stirred solution of sodium nitrite (38.0 gms, 0.551 mol) and 1,7-heptane diol (25.0 g, 0.189 mol) in water (250 ml) at room temperature. After complete addition of the 4N HCl, the reaction mixture was cooled (ice/water bath) and concentrated sulfuric acid (27 ml) was added dropwise. The funnel containing the sulfuric acid was loosely stoppered to avoid seepage of the nitrous acid generated in the reaction mixture. After complete addition of the sulfuric acid, the two-phased solution was stirred 10–15 minutes with cooling and then decanted. The top oily layer was separated, diluted with methylene chloride (100 ml) and washed with a saturated solution of sodium bicarbonate (200 ml). The organic phase was separated, dried (anhydrous $Na_2SO_4$), filtered and concentrated in vacuo. The oily residue obtained was distilled under high vacuum to afford the product, 1,7-heptane dinitrite, as a yellow oil (32.1 g, 89%); b.p. 75°–77° C. (1.5 mm Hg).

Elemental analysis for $C_7H_{14}N_2O_4$:
 Calculated: C-44.21%; H-7.42%; N-14.73%
 Found: C-44.48%; H-7.48%; N-14.44%

EXAMPLE 2

Preparation of 1,5-pentane Dinitrite

The procedure of Example i was followed utilizing 1,5-pentane diol (20g, 0.192 mol) in place of the 1,7-heptane diol.

EXAMPLE 3

Preparation of 1,3-propane Dinitrite

The procedure of Example 1 was followed utilizing 1,3-propane diol (15 g, 0.197 mol) in place of the 1,7-heptane diol.

EXAMPLE 4

Topical Composition

A 5% topical ointment of isoamyl nitrite was prepared in a base of white petrolatum and paraffin wax. The composition contained about 15 mg of nitrite per one inch dose (300 mg) of ointment.

EXAMPLE 5

Parenteral Composition

A parenteral solution of 1,7-heptane dinitrite suitable for intracavernosal injection was prepared with about 0.05 mg (50 μg) of nitrite per injectable dose of 0.2 ml.

EXAMPLE 6

Intracavernosal Injection of Nitrites in Rats

Description of Rat Model

Rats are anesthetized with a long-acting barbiturate (Inactin), and a catheter is inserted in the left femoral artery for the measurement of systemic blood pressure. The penile area is exposed and a needle is inserted in the corpus cavernosal area (the right crus) for the measurement of intracavernosal pressure, and for intracavernosal injection of drugs.

The determination of rat "erection" is through the measurement of cavernosal pressure. In humans and animals the pressure is initially very low (approx. 5–10 mmHg), and during erection it rises to 60–90% of systemic blood pressure (depending on the species and needle placement).

Test Procedure

Four groups of laboratory rats (n=4–7 in each group) were catheterized as described above and baseline cavernosal and arterial blood pressure values were determined. The test animals received intracavernosal injections of nitroglycerin or organic nitrite in ethanol solution in varying molar concentrations. The four groups received, respectively, nitroglycerin (Group 1); 1,5-pentane dinitrite or ethanol solution as placebo (Group 2); 1,7-heptane dinitrite or ethanol placebo (Group 3); and isoamyl nitrite or ethanol placebo (Group 4).

The maximum changes in cavernosal and arterial blood pressure were determined for each animal.

Results

The mean changes in cavernosal and arterial blood pressure of the four test groups are reflected in FIGS. 1–4, respectively. As reflected in FIG. 1, injection of nitroglycerin caused relatively small, dose-dependent increases in intracavernosal pressure, and simultaneously caused almost equivalent systemic ("downstream") reductions in arterial blood pressure (i.e., over 30 mmHg at the highest dose used).

Figure 2:
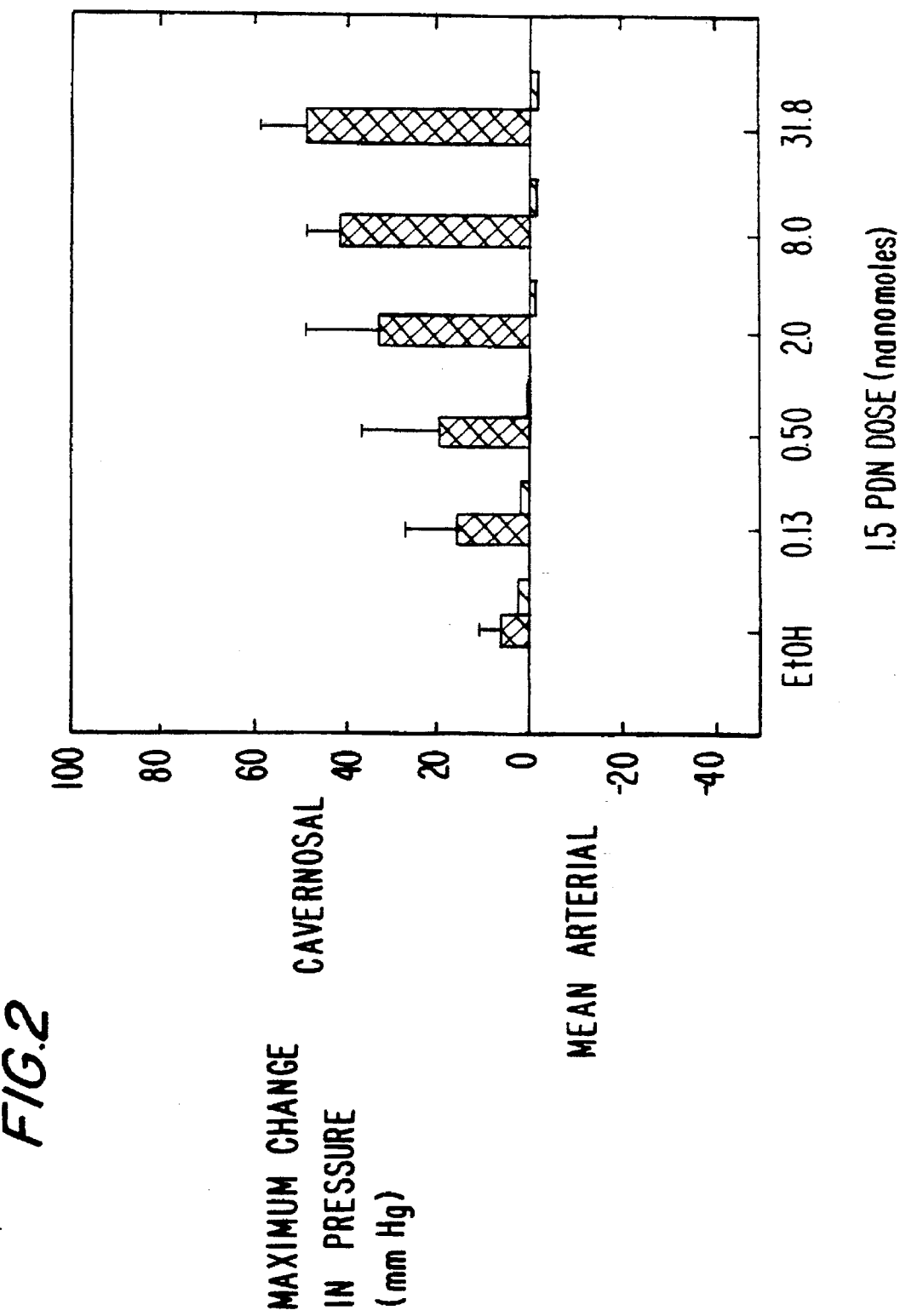
FIG. 2 is a bar graph illustrating the effects of intracavernosal injection of 1,7-heptane dinitrite (1,7 HDN) in anesthetized rats on cavernosal blood pressure and arterial blood pressure (as measured in the left femoral artery).
Figure 3:
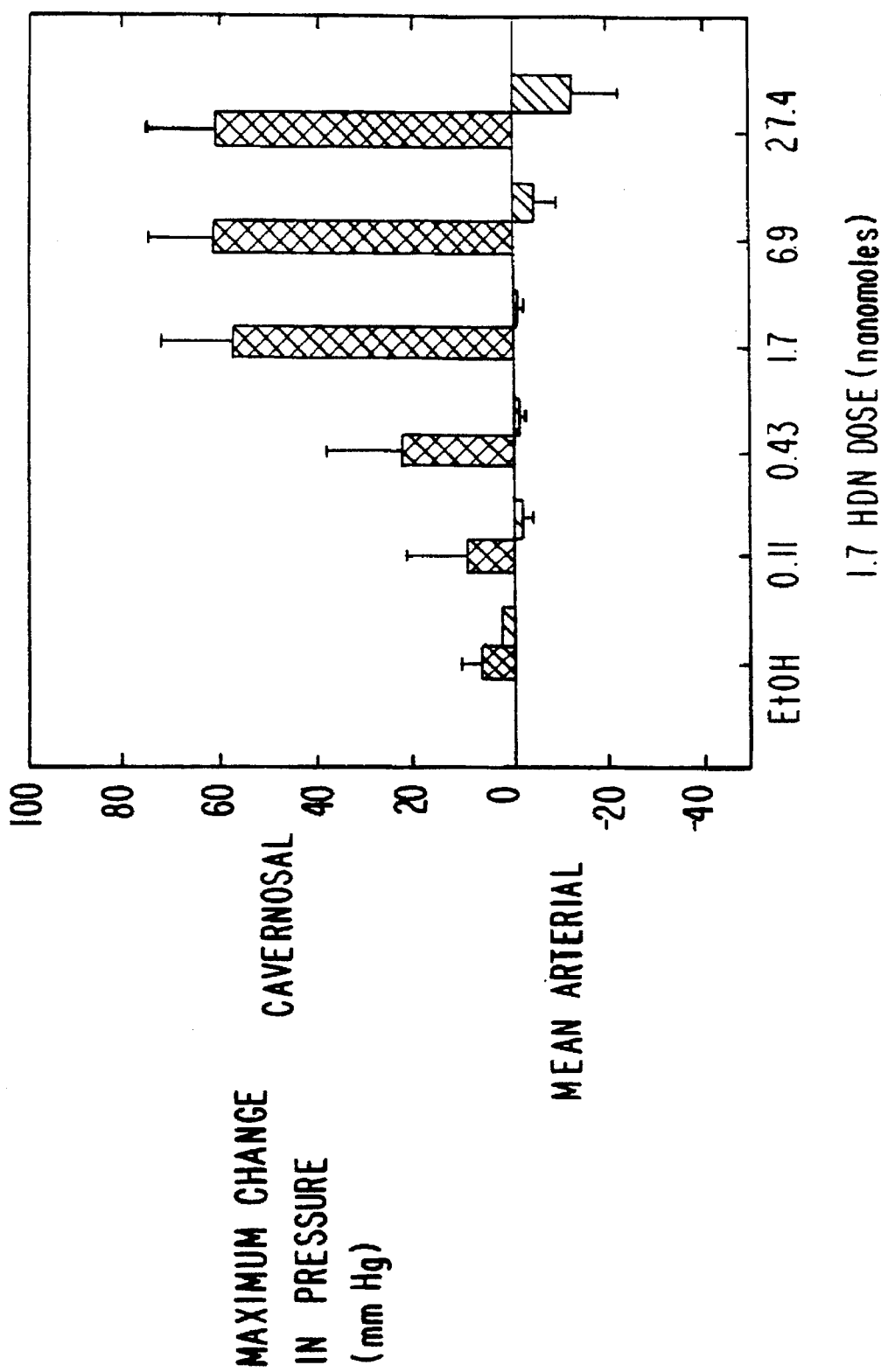
FIG. 3 is a bar graph illustrating the effects of intracavernosal injection of 1,5-pentane dinitrite (1,5 PDN) in anesthetized rats on cavernosal blood pressure and arterial blood pressure (as measured in the left femoral artery).
Figure 4:
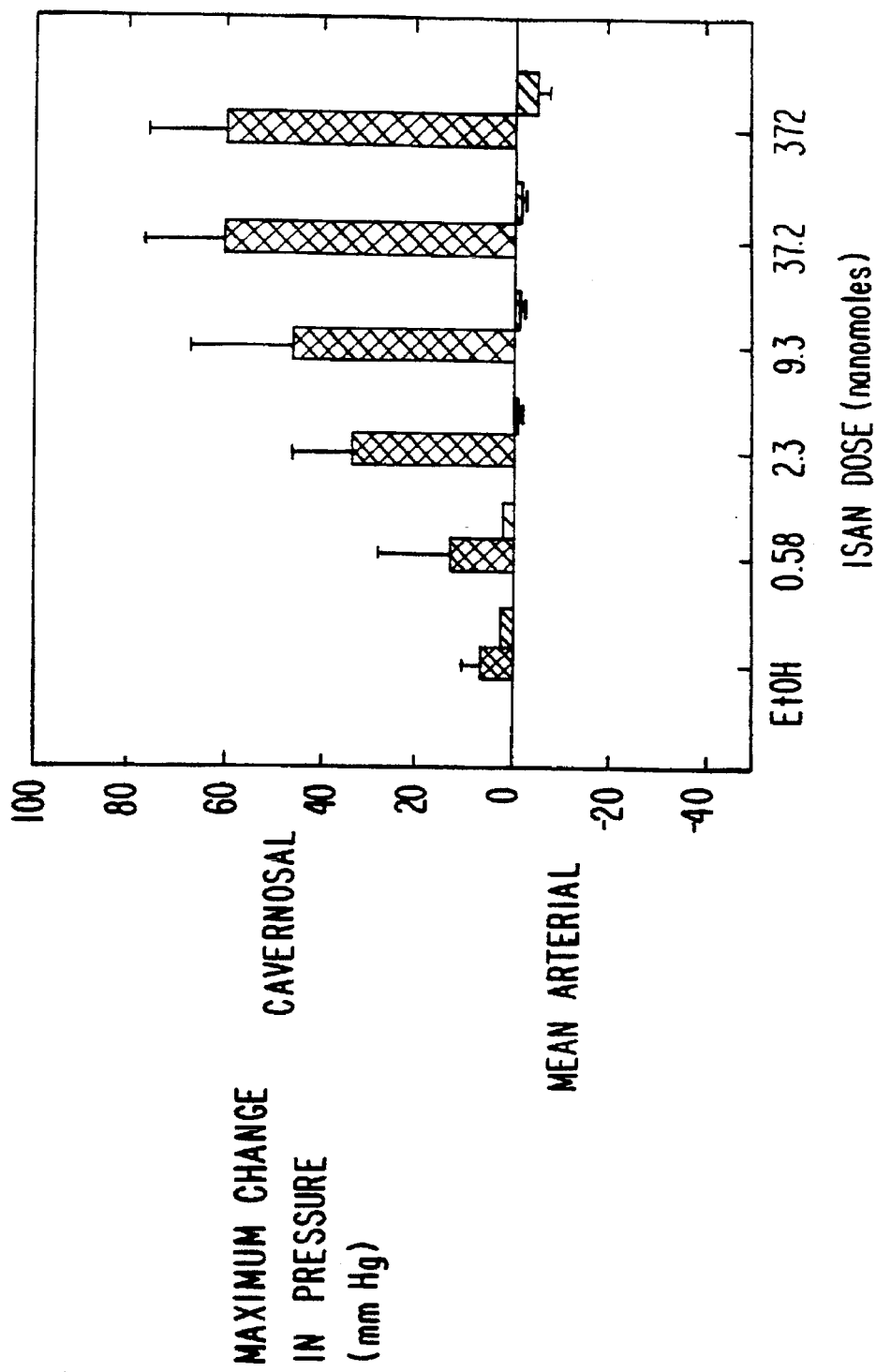
FIG. 4 is a bar graph illustrating the effects of intracavernosal injection of isoamyl nitrite (ISAN) in anesthetized rats on cavernosal blood pressure and arterial blood pressure (as measured in the left femoral artery).

By contrast, as reflected in FIGS. 2–4, injection of organic nitrites caused greater changes in mean intracavernosal pressure in the test subjects while having little or no effects on systemic blood pressure.

EXAMPLE 7

Topical Application of Nitrites in Guinea Pigs

Test Procedure

Ten male outbred Hartley guinea pigs were weighed and placed into treatment groups as follows:

| Group | N | Treatment | Dose |
| --- | --- | --- | --- |
| A1 | 1 | 1,5-pentane dinitrite | 1 μL |
| A2 | 1 | 1,5-pentane dinitrite | 5 μL |
| A3 | 1 | 1,5-pentane dinitrite | 20 μL |
| B1 | 1 | 1,7-heptane dinitrite | 1 μL |
| B2 | 1 | 1,7-heptane dinitrite | 5 μL |

-continued

| Group | N | Treatment | Dose |
| --- | --- | --- | --- |
| B3 | 1 | 1,7-heptane dinitrite | 20 µL |
| C1 | 4 | amyl nitrite | 5 µL |
| C2 | 4 | amyl nitrite | 20 µL |
| D1 | 4 | nitroglycerin (2%) | 1 mg |
| D2 | 4 | nitroglycerin (2%) | 4 mg |

The animals were placed in dorsal recumbency and held in place by restraints. The penis was extruded from the prepuce. Care was taken to not manipulate the penis. Length and diameter measurements were made using digital calipers. The length measurement was taken from the prepuce to the tip of the glans when the penis was extended. The diameter was taken 0.5 cm proximally from the tip of the glans.

The appropriate amount of test material was applied with a Wiretrol™ pipette to the base of the exposed penis. When application was complete, a timer was started. Measurements were taken at 0, 1, 2, 5, 10 and 15 minutes after application or until detumescence was observed.

Results

Figure 5:
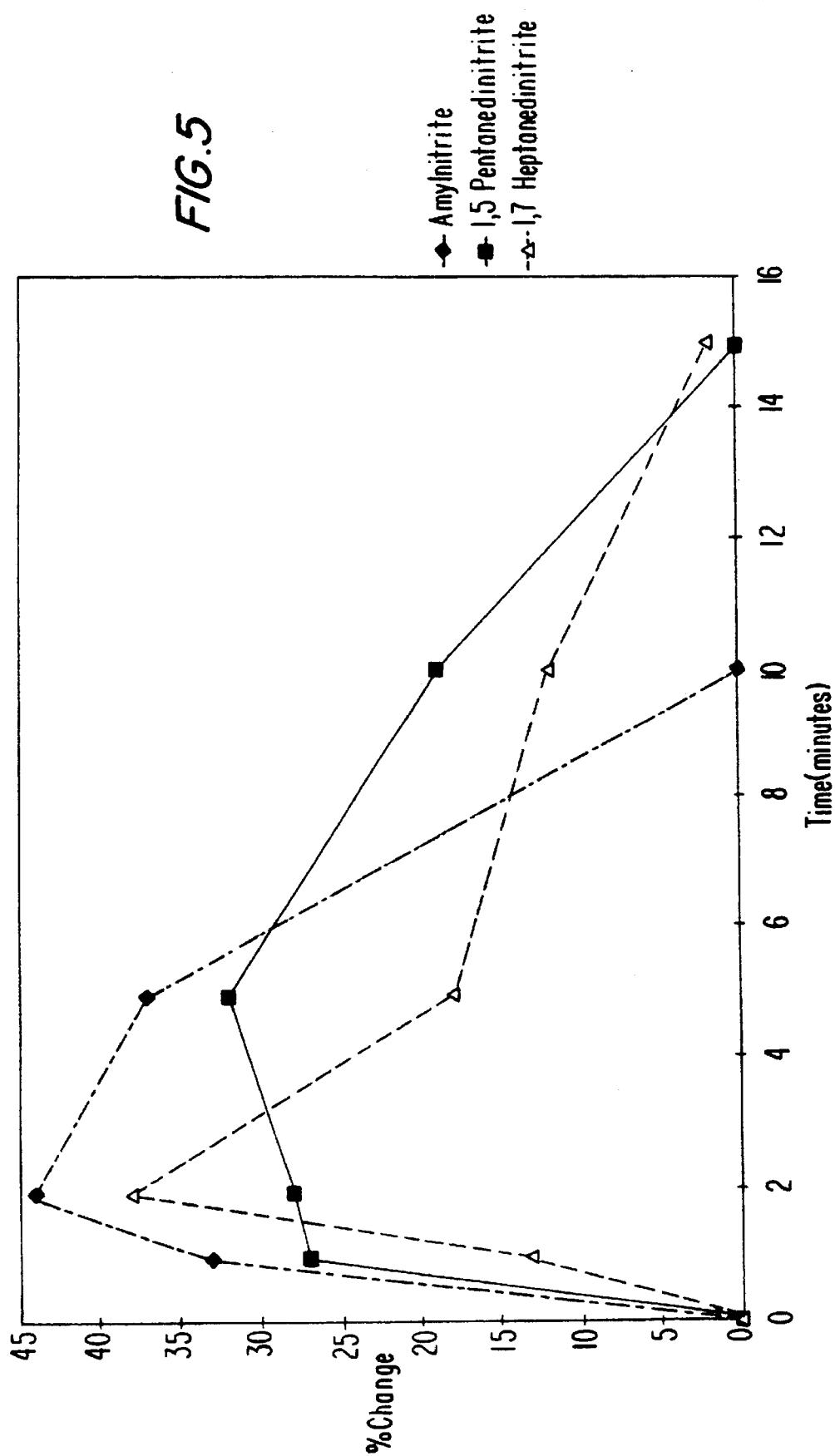
FIG. 5 is graph illustrating the percent increase in penile length in conscious guinea pigs following respective topical application of a 20 µl dose of isoamyl nitrite, 1,5-pentane dinitrite or 1,7-heptane dinitrite.
Figure 6:
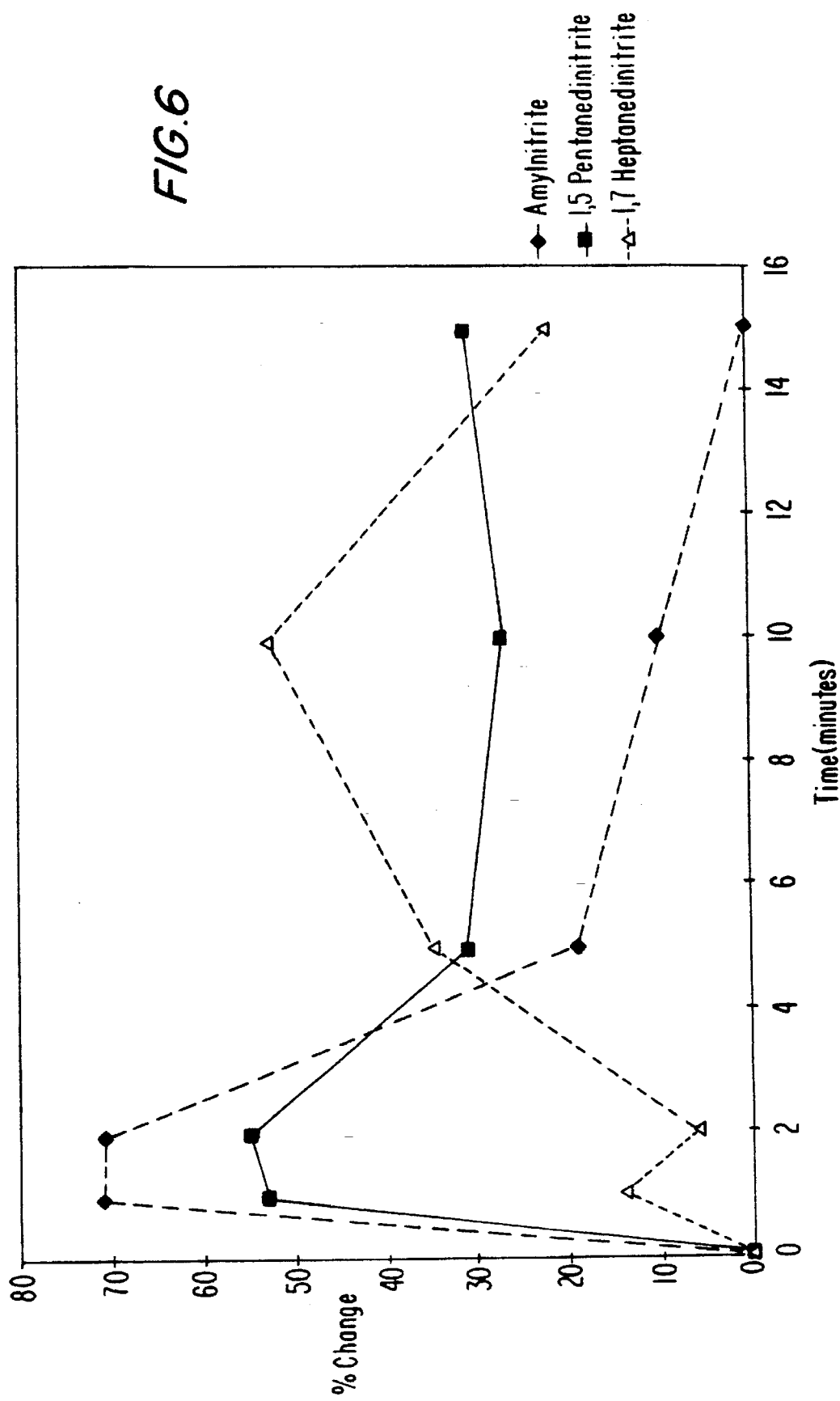
FIG. 6 is graph illustrating the percent increase in penile diameter in conscious guinea pigs following respective topical application of a 20 µl dose of isoamyl nitrite, 1,5-pentane dinitrite or 1,7-heptane dinitrite.
Figure 7:
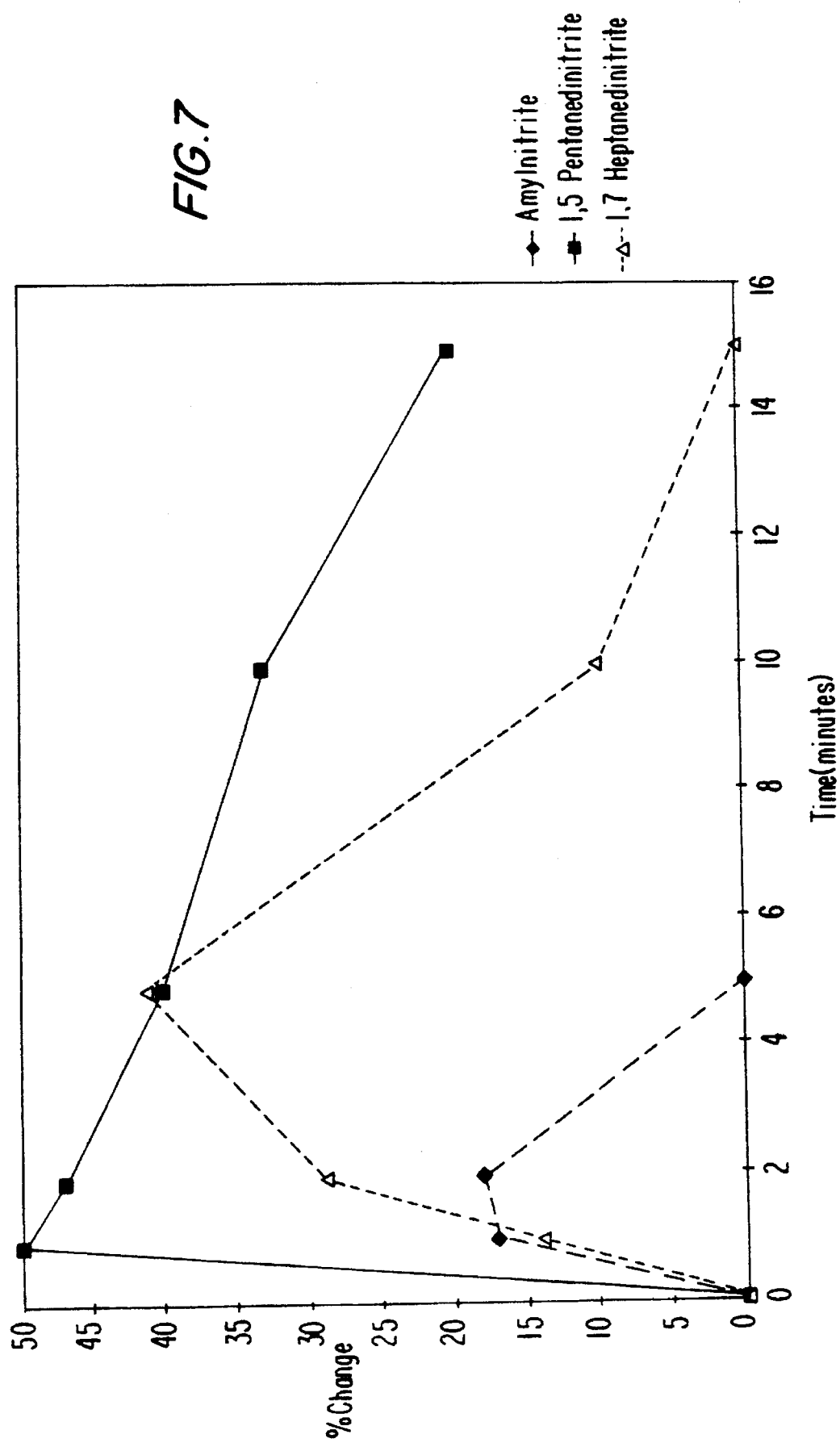
FIG. 7 is graph illustrating the percent increase in penile length in conscious guinea pigs following respective topical application of a 5 μl dose of isoamyl nitrite, 1,5-pentane dinitrite or 1,7-heptane dinitrite.
Figure 8:
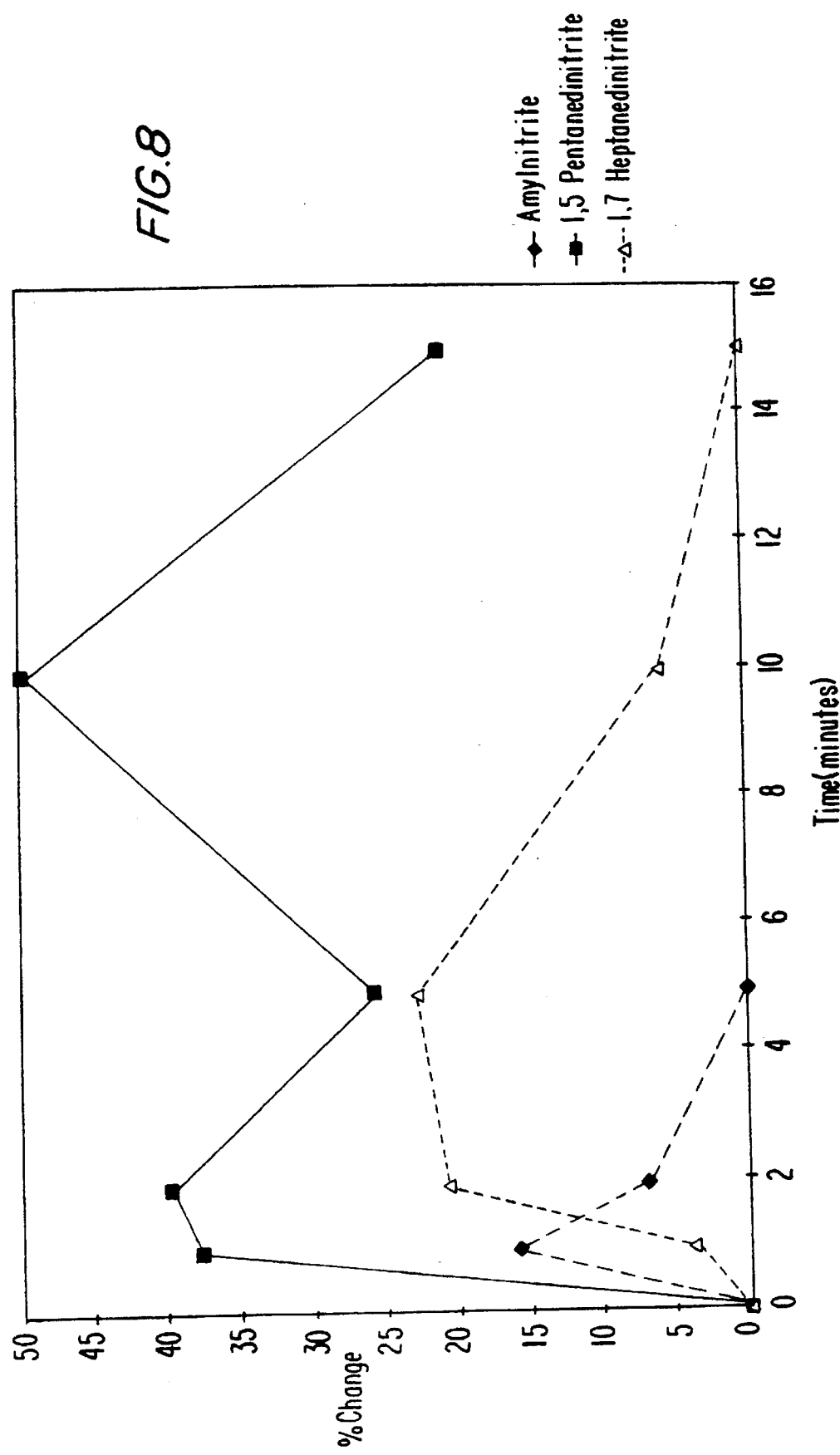
FIG. 8 is graph illustrating the percent increase in penile diameter in conscious guinea pigs following respective topical application of a 5 μl dose of isoamyl nitrite, 1,5-pentane dinitrite or 1,7-heptane dinitrite.
Figure 9:
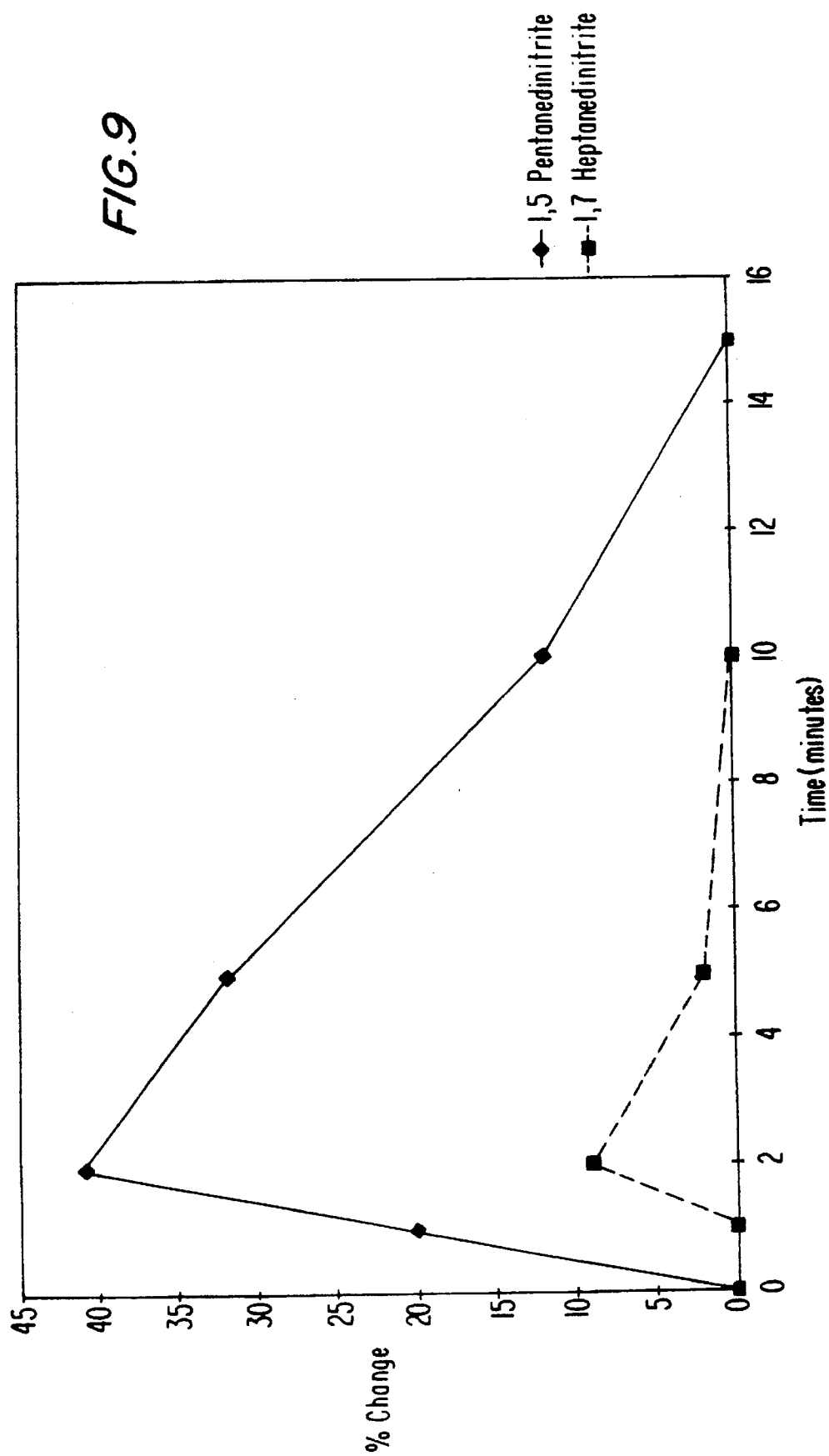
FIG. 9 is graph illustrating the percent increase in penile length in conscious guinea pigs following respective topical application of a 1 μdose of 1,5-pentane dinitrite or 1,7-heptane dinitrite.
Figure 10:
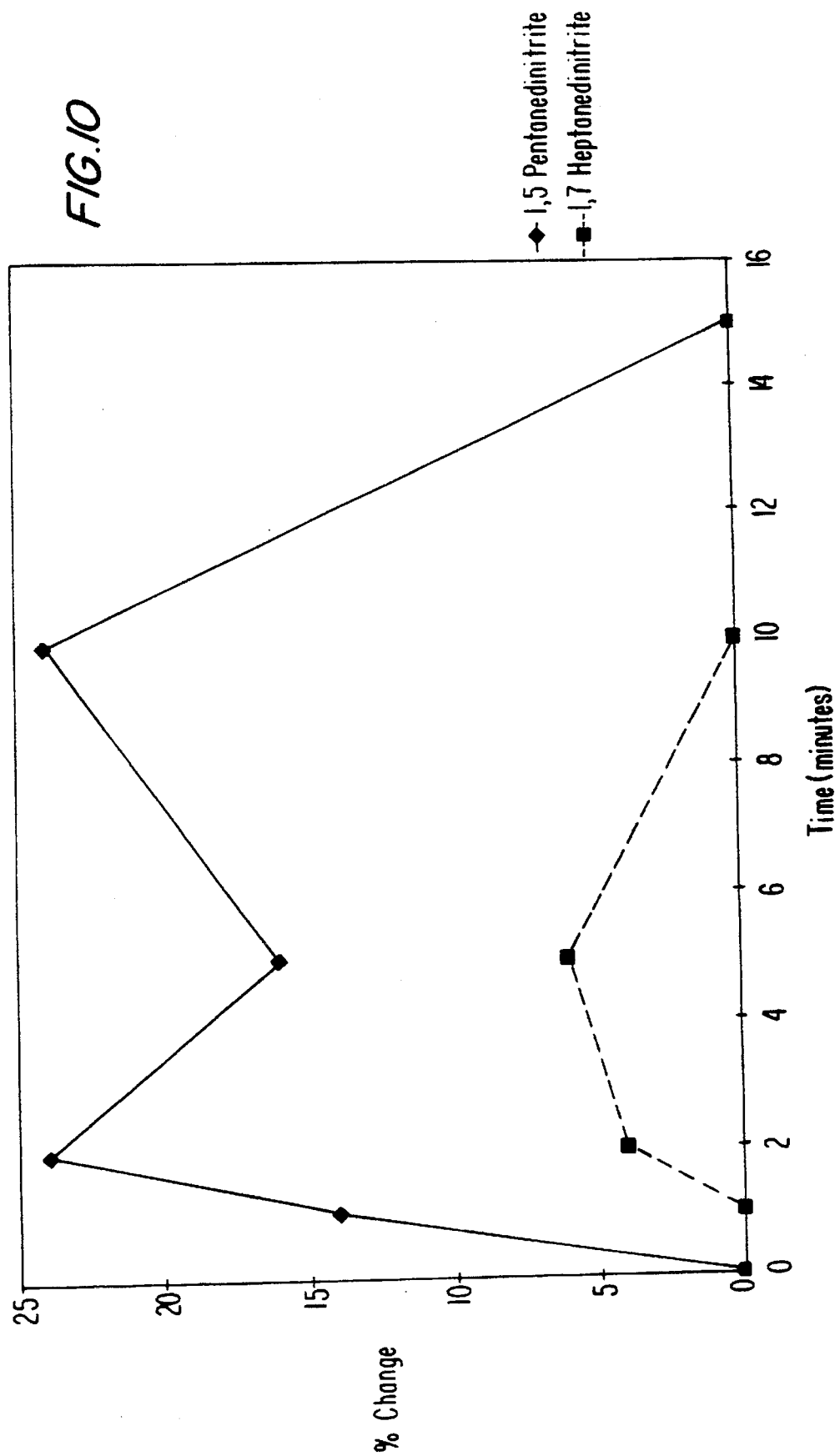
FIG. 10 is graph illustrating the percent increase in penile diameter in conscious guinea pigs following respective topical application of ointments containing a 1 μl dose of 1,5-pentane dinitrite or 1,7-heptane dinitrite.

Data collected during this study are graphically represented in FIGS. 5–13. Inspection of the data indicates that all three of the nitrite compounds were effective at a topical dose of 20 µL. At the 20 µL dose amyl nitrite was slightly more effective than the dinitrite compounds. At the 5 µL dose the data indicate that the 1,5-pentane dinitrite was clearly more effective than the other two compounds (FIGS. 5–6). Due to its poor response at the 5 µL dose, amyl nitrite was not evaluated at 1 µL. At the 1 µL dose 1,5-pentane dinitrite was more effective than the 1,7-heptane dinitrite.

The penis of the guinea pig is classified as mucocutaneous tissue. The glans is covered primarily with keratinized scales. During erection a pouch at the tip of the glans is everted. This pouch contains two horny styles. In all nitrite-treated animals, the eversion of the pouch was observed. This indicated that for the amyl nitrite, 1,5-pentane dinitrite and 1,7-heptane dinitrite, a true erection was produced.

It is believed that the organic nitrites are particularly well-suited for treatment of male impotence and erectile dysfunction because of their ability to provide local cavernosal vasodilation with little systemic vasodilation. They also have the valuable attribute for topical purposes of rapid penetration upon local application.

It has thus been shown that there are provided compositions and methods which achieve the various objects of the invention and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

What is claimed as new and desired to be protected by Letters Patent is set forth in the following claims.

We claim:

1. A pharmaceutical composition for the treatment of male impotence or erectile dysfunction comprising a sufficient amount of an organic nitrite in a pharmaceutically acceptable topical carrier to provide about 0.1 mg–20 mg of nitrite per dose applied to the penis, said nitrite being selected from the group consisting of 1,3-propane dinitrite, 1,5-pentane dinitrite, 1,7-heptane dinitrite, cyclohexylmethyl nitrite, 2-phenylethyl nitrite, 3-chloro-2,2-dimethylpropyl nitrite, tertamyl nitrite, 2-methyl-2-hexyl nitrite, hexyl nitrite, 2-methyl-1,3-propane dinitrite, 2,2,dimethyl-1,3-propane dinitrite, 2-methyl-2-propyl-1,3-propane dinitrite, 2-methyl-2-propyl-1,3-propane dinitrite, 3-hexyl nitrite, octyl nitrite, 4-methyl-2-pentyl nitrite, 4-methyl-1-pentyl nitrite, 2-heptyl nitrite, 3-octyl nitrite, 2-methyl-2-pentyl nitrite, 5-methyl-2-hexyl nitrite, 6-methyl-2-heptyl nitrite, glyceryl dinitrite, glyceryl mononitrite, isosorbide 5-mononitrite, isoidide 5-mononitrite, isomannide 5-mononitrite, pentaerythrityl mononirite, pentaerythrityl dinitrite, pentaerythrityl trinitrite and pentaerythrityl tetranitrite.

2. A composition according to claim 1 which comprises about 15 mg of nitrite per dose.

3. A composition according to claim 1 wherein said dose comprises about 50–500 mg of topical composition.

4. A pharmaceutical composition for the treatment of male impotence or erectile dysfunction comprising a sufficient amount of an organic nitrite in a pharmaceutically acceptable parenteral carrier to provide about 0.01–0.75 mg of nitrite per dose injected into the penis, said nitrite being selected from the group consisting of 1,3-propane dinitrite, 1,5-pentane dinitrite, 1,7-heptane dinitrite, cyclohexylmethyl nitrite, 2-phenylethyl nitrite, 3-chloro-2, 2dimethylpropyl nitrite, tert-amyl nitrite, 2-methyl-2-hexyl nitrite, hexyl nitrite, 2-methyl-1,3-propane dinitrite, 2,2, dimethyl-1,3-propane dinitrite, 2-methyl-2-propyl-1,3-propane dinitrite, 2-methyl-2-propyl-1,3-propane dinitrite, 3-hexyl nitrite, octyl nitrite, 4-methyl-2-pentyl nitrite, 4-methyl-1-pentyl nitrite, 2-heptyl nitrite, 3-octyl nitrite, 2-methyl-2-pentyl nitrite, 5-methyl-2-hexyl nitrite, 6-methyl-2-heptyl nitrite, glyceryl dinitrite, glyceryl mononitrite, isosorbide 5-mononitrite, isoidide 5-mononitrite, isomannide 5-mononitrite, pentaerythrityl mononirite, pentaerythrityl dinitrite, pentaerythrityl trinitrite and pentaerythrityl tetranitrite.

5. A composition according to claim 4 wherein said dose comprises about 0.1–0.5 ml of parenteral composition.

6. A composition according to claim 1 wherein said nitrite is selected from the group consisting of 1,3-propane dinitrite, 1,5-pentane dinitrite and 1,7-heptane dinitrite.

7. A composition according to claim 4 wherein said nitrite is selected from the group consisting of 1,3-propane dinitrite, 1,5-pentane dinitrite and 1,7-heptane dinitrite.

* * * * *